United States Patent [19]

Cohen

[11] 4,136,160

[45] Jan. 23, 1979

[54] SPECIFIC ASSAY FOR ACTIVE DEMYELINIZATION

[76] Inventor: Steven R. Cohen, 6923 Fieldcrest Rd., Baltimore, Md. 21215

[21] Appl. No.: 825,238

[22] Filed: Aug. 17, 1977

[51] Int. Cl.$^2$ .................... G01N 33/16; A61K 43/00
[52] U.S. Cl. .................................. 424/1; 23/230 B; 206/569; 424/12
[58] Field of Search ................. 424/1, 12; 23/230 B; 206/569

[56] References Cited

PUBLICATIONS

Day et al., Chemical Abstracts, vol. 82, No. 7, Feb. 17, 1975, p. 305, Abstract No. 41695s.
Schmid et al., Chemical Abstracts, vol. 82, No. 9, Mar. 3, 1975, p. 240, Abstract No. 53678b.
Thompson, Br. Med. Bull., vol. 33, No. 1, Jan., 1977, pp. 28–33.
Bruno, New Techniques in Tumor Location and Radio-Immunoassay, Ed. Croll et al., J. Wiley & Sons, NY, 1974, pp. 9–15.

Primary Examiner—Leland A. Sebastian
Assistant Examiner—Christine M. Nucker
Attorney, Agent, or Firm—Laff, Whitesel & Rockman

[57] ABSTRACT

A specific test for active demyelinzation is based on a discovery that free myelin basic protein can be detected in cerebrospinal fluid by the use of a radioimmunoassay, and that the level of basic protein found corresponds to the activity of demyelinating pathologies. A simple method is utilized, wherein samples of cerebrospinal fluid are assayed and the results of the assay are compared with standard samples of myelin basic protein. Patients with active demyelinating diseases have high levels (17–100ng/ml) of basic protein; those with progressive pathologies have less (6–16 ng/ml); and those in remission have less than 4 ng/ml, comparable to the control population.

9 Claims, 2 Drawing Figures

FIG. 1

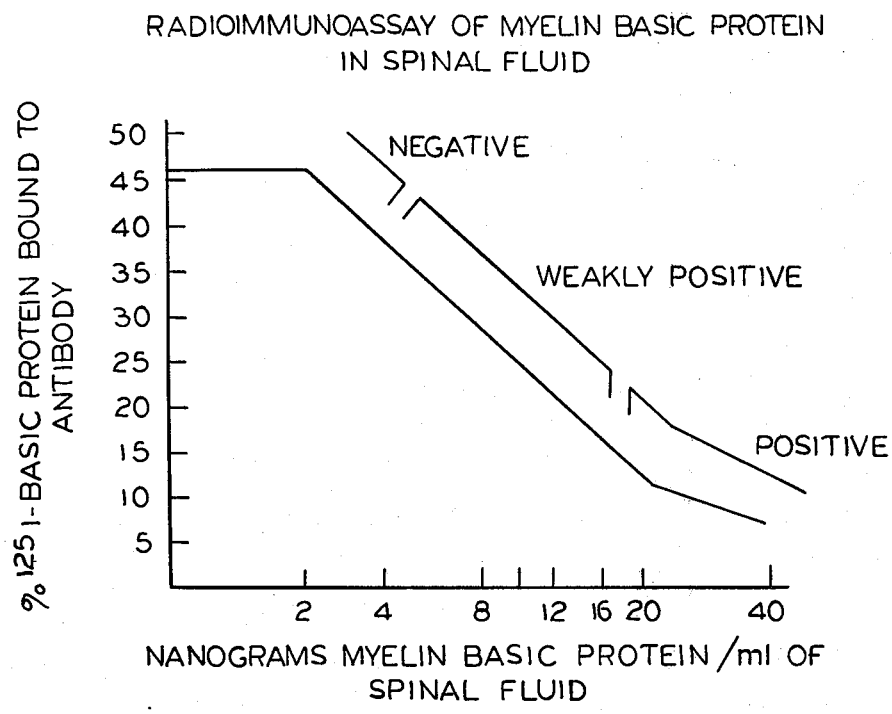

The displacement of $^{125}$I-labeled basic protein from its antibody by increasing amounts of unlabeled purified basic protein is shown. The percent binding for the spinal fluid sample is compared to this standard curve to obtain the amount of basic proteins present in nonograms per ml. The curve is linear between 4 and 20 ng of basic protein per ml of spinal fluid. The categories for negative, weakly positive, and positive are shown.

FIG. 2

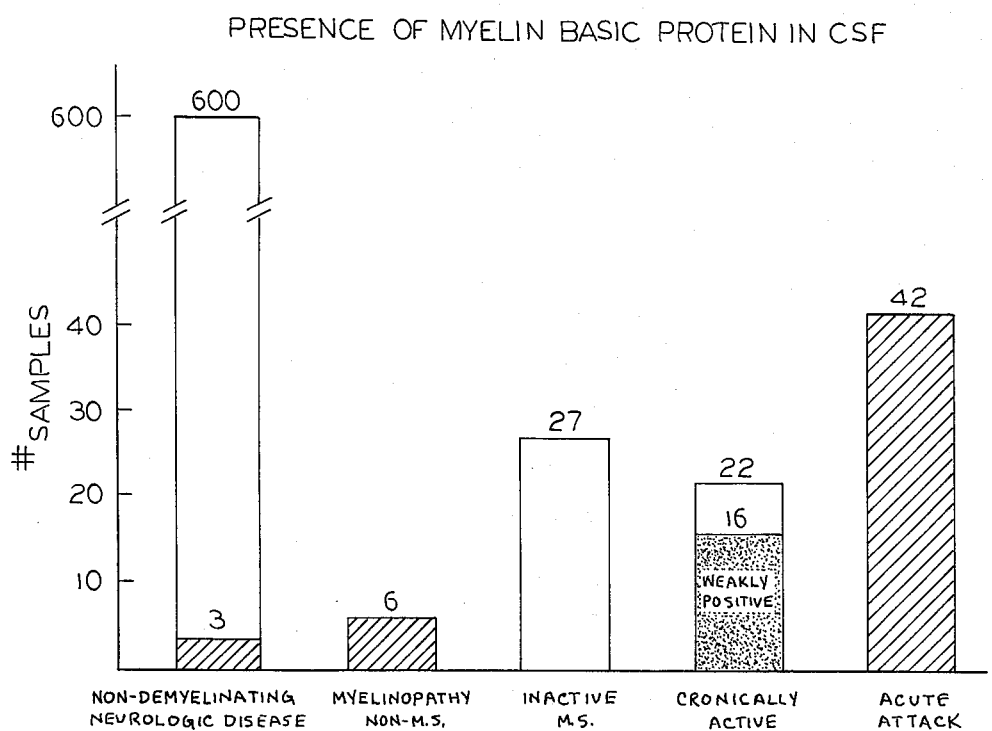

The shaded area represents the number of samples in each group with myelin basic protein in the CSF. The non-demyelinating neurologic diseases included: neuroblastoma, arthrogryposis, temporal arteritis, collagen vascular disease, peripheral neuropathy, cerebellar degeneration, microcephaly, neurosyphilis, seizures, Guillain-Barre syndrome, unknown neuronal disease, trigeminal neuralgia, spastic paraplegia, malignant lymphoma, alcohol withdrawal, dementia, stroke, meningitis, migraine, moya-moya syndrome, progressive supranuclear palsy, motor neuron disease, glue sniffing neuropathy, aneurysm, hydrocephalus, vasculitis, labryinthitis.

SPECIFIC ASSAY FOR ACTIVE DEMYELINIZATION

This invention relates to the specific assay of active demyelinization and more particularly in cerebrospinal fluid for the clinical evaluation of active demyelination. The invention provides a reliable and expedient means of monitoring active demyelinating pathologies by assaying the concentration of myelin basic protein in cerebrospinal fluid.

Many diseases and pathologies of the human body are associated with the destruction of myelin, a lipidprotein membrane that surrounds and protects components of the central nervous system. One of the degredation products of demyelinization is a protein known as myelin basic protein. This protein accounts for as much as thirty percent of the protein found in myelin and may be its major structural protein.

Myelin basic proteins from various animal species have been purified and their amino acid sequences have been determined. The protein consists of a single chain of 170 amino acids whose sequence is very similar in different species. It is an unusual protein in that it has no disulfide bridges, no secondary helical structure, and does not assume a globular structure in solution. Metabolic studies with the basic protein have involved tissue extraction, electrophoretic separation, and optical measurements to quantitate the protein. (Eng, Chao, Gersth, Pratt and Favastijerna, 7 Biochemistry 4455-4465 (1968)).

Immunological techniques have also been used to measure basic protein. (McPherson, Carnegie, *Radioimmunoassay With Gel Filtration for Detecting Antibody to Basic Protein of Myelin*, 72 J. Lab. & Clin. Med. 824-831 (1968)).

Recently, a radioimmunoassay for the myelin basic protein has been developed as a marker for myelin extracted from rat brain tissue, which has been shown to be specific, quantitative, and sensitive to as little as 2 ng. of basic protein. (Cohen, Guarnieri, McKhann, *A Radioimmunoassay for Myelin Basic Protein and its Use for Quantitative Measurements*, J. Neurochemistry, 371-376 (1975)).

One of the major demyelinating diseases suffered by man is multiple sclerosis. In mutliple sclerosis, patches of destroyed myelin are replaced by scar tissue that interrupts and distorts the flow of nerve impulses. At the present time, there is no known cure for multiple sclerosis and there is virtually no therapy that can be used against it. Moreover, there are no reliable tests to diagnose or assess the clinical activity of the disease.

The diagnosis of multiple sclerosis depends primarily on clinical criteria. The four major approaches that have been taken in the search for a specific diagnostic test includes studies on: (1) lymphocytes (Strandgaard, Jorgenson, *Delayed Hypersensitivity to Myelin Antigen in Multiple Sclerosis Investigated With the Leucocyte Migration Method*, Acta Neurol Scand. 243-248 (1972); McPherson, Libura, Seland, *Binding of 125I Labeled Encephalitogenic Basic Protein to Normal Lymphocytes*, 19 Clin. Exp. Immunol., 451-458 (1975); Levy, Auerbach, Hayes, *A Blood Test for Multiple Sclerosis Based on the Adherence of Lymphocytes to Measles Infected Cells*, 294 New Engl. J. Med., 1423-1427 (1976)); (b 2) demyelinating properties of serum (Lumsden, *The Immunogenesis of the Multiple Sclerosis Plague*, 28 Brain Res., 365-390 (1971)); (3) changes in the chemical composition of the CSF (McAlpine, Lumsden, Acheson, *Multiple Sclerosis, A Reappraisal*, 368-432 (second edition, 1972)); as well as (4) radioimmunoassay of antibodies to myelin basic protein (Lennon and McKay, *Binding of Myelin Basic Protein by Serum and Cerebrospinal Fluid*, Clin. Exp. Immunol., 595-602 (1972)) and a cerebrospinal fluid inhibitor cross reactive with myelin basic protein. (McPherson, Gilpin, Selaied, *Radioimmunoassay of CSF for Encephalitogenic Basic Protein: A Diagnostic Test for M.S.?*, 107, Canad. Med. Assoc. J., 856-859 (1972)).

These tests have been concerned with diagnosis of the disease rather than assessment of clinical activity. None has yet proved entirely effective as a diagnostic tool, and none of the tests which are partially successful have any application to monitor the course of the disease.

One proposed test is based upon the observation that leukocytes from multiple sclerosis patients adhere to measles-infected human epithelial cells (in the absence of blood serum) much more strongly than to cells from healthy individuals or from patients with other diseases. However, this test is not yet established, and the phenomena upon which it is based is contradicted by observations of other investigators. See, Levy, et al., 295 New England Journal of Medicine, 732 (1976).

Another proposed procedure is based upon the observation that multiple sclerosis may involve a defect in the functioning of unsaturated fatty acids in cellular membranes. The test involves the migration of macrophages in an electric field. When human leukocytes are exposed to an antigen to which they are sensitized, they release a substance that slows the migration of macrophages from healthy guinea pigs. It has been reported that leukocytes from multiple sclerosis patients release more of this substance, and cause the migration of macrophages to be slowed more markedly than by leukocytes from healthy individuals and patients with other neurological diseases. However, this test is difficult to perform accurately and requires at lest 8 to 10 days to obtain a result. Moreover, the test is complicated, sensitive to slight alterations, and has not yet been consistently reproduced.

A third test involves the migration of lymphocytes in an electric field. It has been observed that lymphocytes from multiple sclerosis patients migrate significantly more slowly than do those from healthy individuals. Lymphocytes from patients with other neurological diseases appear to migrate significantly faster. This test has not yet been reproduced. Moreover, even if it developed into a reliable diagnostic test, it would not appear to have any use as a clinical test to monitor demyelinating activity.

Early studies on the cerebrospinal fluid of multiple sclerosis patients revealed the presence of elevated levels of protein and/or IgG. However, patients with non-demyelinative neurologic disease also had increased levels of cerebrospinal fluid protein and/or IgG; and in no case did the values fluctuate with the activity of the disease.

Electron microscopy has revealed the presence of myelin fragments in cerebrospinal fluid in two out of three cases of active multiple sclerosis. Patients with other neurological diseases and those in remission did not have such fragments in their cerebrospinal fluid. Because of the probable action of proteolytic enzymes on free myelin (Raghavan, Rhoads, Kanfer, *The Effects of Trypsin On Purified Myelin*, 328 Biochimica et Biophysici Acta, 205-212 (1973)), it could not be expected that myelin fragments or myelin basic protein could be identified in cerebrospinal fluid. In fact, in 1971, an assay for free myelin basic protein in cerebrospinal fluid sensitive in the 0.1–1 ug. range was negative. (Lennon and McKay, supra).

The present invention has as a primary objective the provision of a radioimmunological assay for the detection and measurement of myelin basic protein in cerebrospinal fluid. A more particular object is to provide an assay which is quick, easy, and inexpensive to administer, and which is accurate and reliable.

Yet another object of this invention is to provide a method and means for diagnosing and evaluating the clinical progress of multiple sclerosis and other demyelinating pathologies by employing the concentration of myelin basic protein as an indicator of active demyelinization.

Yet another object is to provide such diagnostic and clinical tests that can be inexpensively made and distributed in kits for use in hospitals and other medical centers.

The above mentioned and other features of this invention and the manner of obtaining them will become more apparent, and the invention itself will be best understood by reference to the following description of an embodiment of the invention taken in conjunction with the accompanying drawings wherein:

FIG. 1 is a standard curve for radioimmunoassay of myelin basic protein in spinal fluid; and FIG. 2 is a comparative graph for the presence of myelin basic protein in cerebrospinal fluid samples of patients with mutliple sclerosis, other demyelinating pathologies, and non-demyelinating neurologic diseases.

The method associated with this invention includes the steps of removing cerebrospinal fluid from a patient, and testing it immediately, or storing it frozen until assay. The concentration of myelin basic protein in said sample is then measured by a sensitive radioimmunoassay that can measure as little as 2 ng. of myelin basic protein in cerebrospinal fluid. High levels of basic protein indicate active demyelinating disease, lesser levels indicate progressive demyelinating disease, and median levels comparable to the control population indicate demyelinating disease in remission.

The antigenicity of the myelin basic protein has been well documented. Accordingly, a specific radioimmunoassay for myelin basic protein has recently been developed. This assay has been applied to quantitatively measure myelin in neural tissue and subcellular components by assaying the basic protein as a marker for myelin.

Regarding the assay itself, in the preferred embodiment, 0.05 ml of a concentrated assay buffer (2 M Tris-acetate, pH. 7.5, containing 10 mg/ml of histone) and anitsera at the appropriate concentration is added directly to 0.5 ml of spinal fluid. This mixture is incubated for one hour at 37 degrees C. 5,000 to 20,000 cpm of $^{125}$I-labeled myelin basic protein (sp. act. 2–10 uCi/ug) are added and the mixture is then incubated for one to seventy-two hours at temperatures ranging from 4° C. to 37° C. The antibody-basic protein complex is precipitated with 0.3 to 0.7 ml. of cold ethanol, the pellet and supernatant are separated by centrifugation, and each is assayed for radioactivity, using a Gamma counter or other means for detecting gamma radiation. The percentage of $^{125}$I basic protein bound is the determined and the results are compared to a standard curve. Patients with active demyelinating disease will have high levels of basic protein in the range of 17–100 ng. of basic protein per ml. of cerebrospinal fluid, those with progressive demyelinating disease will have lower levels of basic protein in the range of 6–16 ng. of basic protein per ml. of cerebrospinal fluid, and patients in remission will have less than 4 ng. of basic protein per ml. of cerebrospinal fluid.

In another embodiment of this invention, 5 ml. of cerebrospianl fluid is lyophilized to dryness, and 0.25 ml. of buffer (0.2M trisacetate, pH. 7.5 containing 1 mg/1ml histone) is added to the dry material. A 20 ul aliquot of this concentrated cerebrospinal fluid extract is then assayed by the above described radioimmunoassay procedure.

In still another embodiment of this invention, the incubation step following the addition of the $^{125}$I labeled myelin basic protein is carried out for 2–3 hours at 37° C.

The above procedures differ significantly from that described in Cohen, et al., supra, in that the substances examined therein were rat brain tissue homogenates, subcellular fractions thereof, or a basic protein standard in a total volume of 500 Ml. of antisera and radioimmunoassay buffer. Thus, the Cohen, et al. assay did not reveal a test on a direct sample of a physiological fluid, or even on a concentrated sample of physiological fluids, but rather on the component structures of normal neurological tissues.

In still another embodiment of this invention, the precipitation step is performed by adding an antibody specific to rabbit gamma globulin, produced in any animal ther than a rabbit, to the antibody basic protein complex. Cohen, et al did not teach that the assay could be carried out at room temperature, in a shorter time span than 18–24 hours. Finally, Cohen et al. did not teach that the assay for myelin basic protein could be carried out using a smaller substrate sample suspended in a more highly concentrated buffer.

Among the different embodiments of the present invention, the discovery that an assay for myelin basic protein can be conducted in a few hours at room temperature is particularly significant. This allows the assay to be of great use and convenience in a clinical setting where the assay to be conducted without the need for refrigeration, and it reduces the expenses otherwise necessary to carry out the assay. Moreover, it was unexpectedly discovered that an assay for myelin basic protein at room temperature could be provided, because the presence in physiological fluids of proteolytic enzymes would be expected to attach and destroy said protein at room temperature.

It is understood that other buffers, temperatures, and incubation periods may be used in place of those specifically mentioned above and still fall within the scope of the present invention.

The present invention is further distinguishable from the disclosure of Cohen, et al., supra, in the application of the radioimmunoassay. The disclosure in the Cohen article referred to a method for investigating the amount of myelin in brain tissue and tissue homogenates. Myelin basic protein was not investigated itself, but was only used as a marker for the presence of myelin. Moreover, free basic protein was not present in the samples studied, but was insted obtained by disruption of myelin by heat, organic solvents, and various detergents. In contrast, the present invention is a method for detecting free basic protein in spinal fluid which has not been degraded or altered in any manner. Instead of using the assay for bound basic protein as a marker for another substance, this invention uses the assay for free basic protein as a method of detecting and evaluating certain pathologies.

Prior to the development of this invention, it was not known if free myelin basic protein was present in cerebrospinal fluid. In fact, it was doubtful that free basic protein could exist in cerebrospinal fluid, because of enzymes which would normally attack and degrade the protein. Early applications of radioimmunoassays on cerebrospinal fluid were negative for myelin basic protein. The present invention is thus a significant advance, in that it quantitatively measures myelin basic protein in cerebrospinal fluid. An even greater advance is the discovery that such measurements can serve as an index of pathologies involving active demyelination.

The present invention is unique as a means for evaluating the activity of demyelinating pathologies. Prior investigations, such as that reported by Levy, et al., supra, focused solely on the diagnosis of specific diseases, such as multiple sclerosis. Moreover, these investigations focused either upon serological phenomena or the physical characteristics of lymphocytes. Similarly, the investigation by McPherson, Gilpin and Seland was directed at an inhibitor in cerebrospinal fluid rather than the presence of basic protein itself. While McPherson, et al., do describe the presence of basic protein in spinal fluid, they reported levels of 200 to 2,000 ng/ml of cerebrospinal fluid, levels much higher than those discovered by the present invention. Moreover, and most significantly, all the multiple sclerosis patients tested by McPherson, et al. reacted identically, independent of whether or not they were in attack.

In contrast, the present method evaluates a product of the demyelinating pathology, myelin basic protein. The results are quantitative and vary directly with the activity of the pathology. Consequently, the present invention can be used both as a diagnostic tool as well as a method to clinically evaluate on-going demyelinating activity. Moreover, unlike other tests which are specific to one disease, the present invention can be used to evaluate the activity of any demyelinating pathology.

The following examples illustrate the application of this invention.

EXAMPLE

Samples of cerebrospinal fluid were taken from 697 patients with a variety of neurological diseases. Spinal fluid samples were stored frozen ($-20°$ C.) until assay. All samples were assayed in a "blind" study, that is, clinical diagnosis for each patient was reported to the laboratory after the sample was assayed. Ninety-one patients had multiple sclerosis, six had other forms of demyelinating pathologies, and the remaining 600 had a variety of other neurological diseases.

The radioimmunoassay described above was performed on each of the 697 samples and on samples of pure myelin basic protein for the purpose of obtaining a standard curve. A typical standard curve is shown in FIG. 1.

On the basis of studies of the amounts of basic protein in more than 697 samples of CSF, three categories were designated as shown in FIG. 1 (less than 4 ng/ml, negative; 5-16 ng/ml, weakly positive; greater than 17 ng/ml, positive). The results are shown in FIG. 2.

FIG. 1

The displacement of $^{125}$I-labeled basic protein from its antibody by increasing amounts of unlabeled purified basic protein is shown. The percent binding for the spinal fluid sample is compared to this standard curve to obtain the amount of basic protein present in nanograms per ml. The curve is linear between 4 and 20 ng of basic protein per ml of spinal fluid. The categories for negative, weakly positive and positive are shown.

FIG. 2

The shaded area represents the number of samples in each group with myelin basic protein in the CSF. The non-demyelinating neurologic diseases included: neuroblastoma, arthrogryposis, temporal arteritis, collagen vascular disease, peripheral neuropathy, cerebellar degeneration, microcephaly, neurosyphilis, seizures, Guillain-Barre syndrome, unknown neuronal disease, tigeminal neuralgia, spastic paraplegia, malignant lymphoma, alcohol withdrawal, dementia, stroke, meningitis, migraine, moya-moya syndrome, progressive supranuclear palsy, motor neuron disease, glue sniffing neuropathy, aneurysm, hydrocephalus, vasculitis, labryinthitis. The myelinopathies are shown in Table 2.

Patients with multiple sclerosis were divided into three categories based on their clinical symptoms. Nineteen patients who were in remission and clinically inactive had no demonstrable basic protein in the CSF. Eleven of thirteen patients who were chronically activite — the slowly progressive form of the disease — had low levels of myelin basic protein in the CSF. All fifteen patients in acute exacerbation had very high levels of CSF myelin basic protein.

Table 1 shows data on three MS patients and one with transverse myelitis during, following, and in one case, prior to acute attacks. The level of CSF myelin basic protein drops rapidly following the attack. These three patients all recovered rapidly from their neurological symptoms during this time. A fourth patient whose CSF was not obtained until 7-10 days after the attack also had a low value of basic protein in his CSF even though his symptoms had not improved.

Table 1

| | Changes in Level of CSF Basic Protein Following Acute Attacks of Demyelination | | | |
|---|---|---|---|---|
| | Amount of Myelin Basic Protein in CSF (ng/ml) | | | |
| Patients | Before Attack | Acute Stage | Recovery | Acute Stage |
| Multiple Sclerosis | | | | |
| A | 8.5 1 month | 60 _14 days_→ | 0 | |
| B | | 60 _10 days_→ | 0 | 6 months 23 |
| C | | 50 _10 days_→ | 0 | |
| D | | 15 _7 days_→ | 10 | |

Table 1-continued

Changes in Level of CSF Basic Protein
Following Acute Attacks of Demyelination

| Patients | Before Attack | Acute Stage | Recovery | Acute Stage |
|---|---|---|---|---|
| E | | 30 —16 days→ | 10 | |
| F | | 38 —10 days→ | 17 | |
| Transverse Myelitis plus Systemic Lupus Erythematosis | | 100 —1 month→ | 13 | |

Of 600 patients with nondemyelinative neurologic disease, three were positive for myelin basic protein in the CSF. Two of these these patients had strokes near the surface of the brain, and the third had radiation neurosis. Tissue damage in these patients was very extensive. Four other patients who were positive for the basic protein in their CSF had myelinopathies, which is a term used to designate a demyelinative process other than multiple sclerosis. These included a case of transverse myelitis, central pontine myelinolysis, metachromatic leukodystrophy, adrenal leukodystrophy, and a child with neurologic symptoms identical with a sister whose autopsy revealed a brain with little or no myelin. These nine "false positives" are shown in Table 2. The data all indicate that radioimmunoassay of cerebrospinal fluid for myelin basic protein is a useful indicator of active demyelination.

Table 2

Levels of Basic Protein in CSF of
Patients Without Multiple Sclerosis

| Neurologic Diseases - nondemyelinative | Basic Protein ng/ml CSF |
|---|---|
| Lateral medullary infarction | 60 |
| Cerebellar infarction | 50 |
| Radition neurosis | 12 |
| Myelinopathies - non Multiple Sclerosis | |
| Transverse myelitis and systemis lupus eruthematosis | 100 |
| "Hereditary leukodystrophy" | 23 |
| Metachromatic leukodystrophy | 12 |
| Central pontine myelinolysis | 50 |
| Adrenal leukodystrophy patient 1 | 8 |
| Adrenal leukodystrophy patient 2 | 10 |

Those skilled in the art will readily perceive changes and modifications which may be made in the disclosed invention. Therefore, the appended claims are to be construed broadly enough to cover all equivalent structures falling within the scope and spirit of the invention.

I claim:

1. A method of conducting a specific assay for active demyelinization comprising the steps of incubating human spinal fluid with a radioactive antisera to myelin basic protein, addition of a known quantity of radioactive myelin basic protein to the inculation mixture, a separation of the bound and free basic protein, and measurement of the radioactivity of the bound and unbound fractions.

2. The method claim 1 wherein said test is performed directly upon samples of unconcentrated cerebrospinal fluid.

3. The method of claim 1 wherein said test is performed upon concentrated samples of cerebrospinal fluid.

4. The method of claim 1 wherein said samples of cerebrospinal fluid are diluted with a buffer containing calf thymus histone.

5. A method of detecting myelin basic protein in body fluids comprising the steps of: (a) withdrawing spinal fluid samples from the body;
   (b) adding Tris-acetate buffers to the fluid sample to achieve a concentration of 1 to 3 molar Tris-acetate in a pH range of pH 7.2 to pH 7.8, the buffer containing histone in the range of 1 to 20 mg. 1ml., and normal serum in the range of 0.25 to 1% and antisera in a concentration that gives 40% to 60% binding of the $^{125}I$ basic protein;
   (c) incubating the mixture for a period of time ranging from one to twenty-four hours at temperatures ranging from 37° C. to 4° C.;
   (d) adding 5,000 to 20,000 cpm. $^{125}I$-labeled myelin basic protein to the mixture;
   (e) incubating this mixture for a period of time ranging from one to seventy-two hours at temperatures ranging from 4° C. to 37° C., forming an antibody-basic protein complex;
   (f) precipitating the antibody-basic protein complex in 0.3 to 0.7 ml. of cold ethanol;
   (g) separating the antibody-basic protein complex from the supernant by centrifugation; and
   (h) assaying the antibody-basic protein complex and supernant for radiation using a radiation detector.

6. The method described in claim 5 wherein 1 to 10 ml. of cerebrospinal fluid is lyophilized to dryness, 0.1 to 1.0 ml. of said buffer diluted tenfold is added to the dry material, and a 10 to 40 ul. aliquot is assayed following the steps of claim 5.

7. The method described in claim 5 wherein the precipitation step is performed by adding an antibody specific to rabbit gamma globulin, produced in any animal other than a rabbit, to the antibody-basic protein complex.

8. A mercantile unit comprising samples of Tris-acetate buffer containing histone and myelin basic protein antisera, said buffer having a pH in the range of 7.2 to 7.8, samples of $I^{125}$-labeled myelin basic protein, and 0.3 to 0.7 ml. samples of ethanol.

9. The merchantile unit claimed in claim 8 wherein samples of an antibody specific to rabbit gamma globulin produced in any animal other than a rabbit is substituted for the 0.3 to 0.7 ml. samples of ethanol.

* * * * *

UNITED STATES PATENT AND TRADEMARK OFFICE
CERTIFICATE OF CORRECTION

PATENT NO. : 4,136,160
DATED : January 23, 1979
INVENTOR(S) : Steven R. Cohen

It is certified that error appears in the above-identified patent and that said Letters Patent are hereby corrected as shown below:

Column 1, line 65, "(b2)" should be --(2)--

Signed and Sealed this

Seventeenth Day of July 1979

[SEAL]

Attest:

LUTRELLE F. PARKER

Attesting Officer   Acting Commissioner of Patents and Trademarks

Disclaimer 4,136,160.—*Steven R. Coh,* Baltimore, Md. SPECIFIC ASSAY FOR ACTIVE DEMYELINIZATION. Patent dated Jan. 23, 1979. Disclaimer filed June 28, 1982, by the inventor.

Hereby enters this disclaimer to claims 1 through 4 of said patent.

*[Official Gazette August 24, 1982.]*